(12) United States Patent
Malachi et al.

(10) Patent No.: US 11,495,337 B1
(45) Date of Patent: Nov. 8, 2022

(54) COMPUTING SYSTEM FOR FULL TEXTUAL SEARCH OF A PATIENT RECORD

(71) Applicant: Allscripts Software, LLC, Raleigh, NC (US)

(72) Inventors: Tzlil Malachi, Beer Sheva (IL); Yoni Levy, Omer (IL)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 510 days.

(21) Appl. No.: 16/712,123

(22) Filed: Dec. 12, 2019

(51) Int. Cl.
*G16H 10/00* (2018.01)
*G16H 10/60* (2018.01)
*G06F 40/143* (2020.01)
*G06F 16/81* (2019.01)

(52) U.S. Cl.
CPC .............. *G16H 10/60* (2018.01); *G06F 16/81* (2019.01); *G06F 40/143* (2020.01)

(58) Field of Classification Search
CPC ........ G16H 10/60; G06F 16/81; G06F 40/143
See application file for complete search history.

(56) References Cited

U.S. PATENT DOCUMENTS

| | | | |
|---|---|---|---|
| 5,832,450 A | 11/1998 | Myers et al. | |
| 6,122,647 A * | 9/2000 | Horowitz | G06F 16/9558 707/999.005 |
| 6,137,911 A | 10/2000 | Zhilyaev | |
| 7,739,123 B1 * | 6/2010 | Rappaport | G16H 50/20 705/2 |
| 8,037,052 B2 * | 10/2011 | Kariathungal | G06F 16/951 707/709 |
| 8,239,216 B2 * | 8/2012 | McCallie, Jr. | G16H 50/70 705/2 |
| 8,898,798 B2 | 11/2014 | Rogers et al. | |
| 10,956,031 B1 * | 3/2021 | Teague | G06F 3/04886 |

(Continued)

OTHER PUBLICATIONS

Yang et al, "Query Log Analysis of an Electronic Health Record Search Engine", AMIA Annu Symp Proc. 2011; 2011: 915-924, 2011, 10 pages.*

(Continued)

*Primary Examiner* — William L Bashore
*Assistant Examiner* — David Faber
(74) *Attorney, Agent, or Firm* — Calfee, Halter & Griswold LLP

(57) ABSTRACT

A server computing device generates a virtual patient object (VPO) from a patient health record. The server computing device generates documents based upon the VPO. The server computing device causes a term-document index to be generated based upon the documents, the term-document index mapping terms in text of the documents to identifiers for the documents in which the terms are found. Subsequently, responsive to receiving a textual query from a client computing device, the server computing device executes a textual search over the term-document index based upon the textual query. The textual search produces search results that comprise an identifier for a document in the documents that includes a term specified in the textual query. The server computing device identifies a portion of the VPO based upon the search results and transmits the portion of the VPO to the client computing device for display.

20 Claims, 8 Drawing Sheets

(56) References Cited

U.S. PATENT DOCUMENTS

| | | | |
|---|---|---|---|
| 11,031,107 B2* | 6/2021 | Liang | G16H 10/20 |
| 11,133,090 B2* | 9/2021 | McCallie, Jr. | G06F 16/313 |
| 2003/0069758 A1* | 4/2003 | Anderson | G16H 40/20 |
| | | | 707/999.102 |
| 2004/0215981 A1* | 10/2004 | Ricciardi | H04L 9/3236 |
| | | | 713/176 |
| 2004/0249667 A1* | 12/2004 | Oon | G16H 10/60 |
| | | | 705/2 |
| 2006/0235881 A1 | 10/2006 | Masarie et al. | |
| 2007/0061393 A1* | 3/2007 | Moore | H04L 67/02 |
| | | | 709/201 |
| 2007/0282633 A1* | 12/2007 | Haider | G16H 10/60 |
| | | | 700/47 |
| 2008/0120296 A1* | 5/2008 | Kariathungal | G16H 10/60 |
| 2008/0195600 A1 | 8/2008 | Deakter | |
| 2008/0281631 A1* | 11/2008 | Syth | G16H 40/67 |
| | | | 705/2 |
| 2010/0131498 A1* | 5/2010 | Linthicum | G06F 16/338 |
| | | | 707/E17.046 |
| 2010/0179827 A1* | 7/2010 | McCallie, Jr. | G16H 50/70 |
| | | | 707/E17.014 |
| 2011/0082794 A1* | 4/2011 | Blechman | G06Q 10/10 |
| | | | 705/50 |
| 2012/0041788 A1* | 2/2012 | Wons | G16H 70/20 |
| | | | 705/3 |
| 2012/0102502 A1* | 4/2012 | Mathur | G06Q 40/08 |
| | | | 719/313 |
| 2015/0012887 A1* | 1/2015 | Ash | G16H 15/00 |
| | | | 715/835 |
| 2015/0379210 A1* | 12/2015 | Serlie | G16H 50/70 |
| | | | 705/3 |
| 2016/0019299 A1* | 1/2016 | Boloor | G06F 16/9535 |
| | | | 705/3 |
| 2016/0110523 A1* | 4/2016 | Francois | G16H 10/20 |
| | | | 705/2 |
| 2016/0140295 A1* | 5/2016 | Powell | G06Q 10/06 |
| | | | 705/3 |
| 2016/0210427 A1* | 7/2016 | Mynhier | G16H 10/60 |
| 2016/0232298 A1* | 8/2016 | Campbell | G06Q 50/22 |
| 2016/0232306 A1* | 8/2016 | Achan | G06F 21/6245 |
| 2018/0018428 A1* | 1/2018 | Coifman | G06F 16/27 |
| 2018/0046764 A1* | 2/2018 | Katwala | G16H 15/00 |
| 2019/0095581 A1* | 3/2019 | Mccallie, Jr. | G06F 16/313 |

OTHER PUBLICATIONS

Martinez et al, "Improving search over Electronic Health Records using UMLS—based query expansion through random walks", Journal of Biomedical Informatics, 2014, 7 pages.*

Shivade et al, "A review of approaches to identifying patient phenotype cohorts using electronic health records", J Am Med Inform Assoc 2014, 2014, 10 pages.*

Plaisant et al, "Searching Electronic Health Records for Temporal Patterns in Patient Histories: A Case Study with Microsoft Amalga", AMIA 2008 Symposium Proceedings, 2008, p. 601-605.*

"A Method and System for Automatically Selecting Patient Cohorts from Electronic Health Records using Flexible Search and an Automatic Longitudinal Patient Record formation", Disclosed Anonymously, An IP.com Prior Art Database Technical Disclosure, IP.com No. IPCOM000241430D, Apr. 25, 2015, 6 pages.*

* cited by examiner

```xml
<?xml version="1.0" encoding="ISO-8859-1"?>
<patientRecord xmlns="http://schemas.XXX.com/data/contracts/v1" xmlns:xi="http://www.w3.org/2001/XMLSchema-instance"
Xmlns:xsd="http://www.w3.org/2001/XMLSchema">
+ <patientIndexes>
- <conditions>
    - <condition lastModified="2018-12-03-T15:12:57.833Z" isPastMedicalHistory="false" isNegated="true"
      conditionType="false" isExportable="true" isActiveIndication="false">
        <id>170315_b4_amb_sample2_v13_ab1791b0-5c71-11db-b0de-0800200c9a66</id>
        <systemID>2.16.840.1.113883.3.57.1.3.5.52.2.80</systemID>
        <identifiableType>Condition</identifiableType>
        <observation>
            -<type text="Problem">
                -<code is PreferredTranslation="true" isBaseline="false">
                    <id>55607006</id>
                    <systemID>2.16.840.1.113883.6.96</systemID>
                    <systemDisplayName>SNOMED-CT</systemDisplayName>
                    <designationValue>Allergy to Pollen</designationValue>
                    <designation defaultValue="Problem">
                        <localizedStrings>
                            <localizedString culture="en-US" value="Problem"/>
                        </localizedStrings>
                    </designation>
```

FIG. 4

SMITH, John | DOB: 09/17/1986 | Male | MRN: 12345

Search: "pollen"

VIEW OPTIONS

EXECUTE SEARCH

» Encounters
» Problems
» Past Medical History
» Diagnoses
» Allergies
» Medications
» Measurements
» Labs
» Pathology
» Immunizations
» Imaging
» Procedures
» Documents John Smith is allergic to pollen.

FIG. 5

COMPUTING SYSTEM FOR FULL TEXTUAL SEARCH OF A PATIENT RECORD

BACKGROUND

Electronic health record applications (EHRs) are computer-executable applications that are configured to assist healthcare workers with providing care to patients. EHRs are configured with functionality pertaining to patient intake, patient billing, insurance billing, prescription generation, maintaining a record of patient care over time, etc. EHRs are often used by healthcare workers at the point of care (i.e., at a time when the healthcare worker is providing care to a patient). For example, a healthcare worker may retrieve data from a patient health record of a patient maintained by an EHR to relatively quickly ascertain problems being experienced by the patient, medications currently being taken by the patient, and so forth.

Typically, patient health records are maintained by an EHR in a relational database. A relational database is a database in which data is organized into tables comprising rows and columns, with a unique key identifying each row. A computing device retrieves data from the relational database using queries (e.g., Structured Query Language (SQL) queries) that specify tables, rows of tables, and/or columns of tables that are to be searched. In an example where a table entitled "Patients" comprises a "PatientID" column, a "PatientName" column, an "Address" column, and a "City" column and where rows of the "Patients" table correspond to different patients, an example SQL query to retrieve rows for patients that are from the city "Greenville" may be "SELECT * FROM Patients WHERE City='Greenville';".

While a SQL query may be manually input by a user, in most cases, healthcare workers using an EHR lack the technical expertise to manually generate SQL queries. As such, the EHR may provide a search bar that enables the healthcare worker to input a term (e.g., "Greenville" in the example above) that they would like to search for in the patient health record. The EHR then automatically constructs a SQL query and executes the query to retrieve portions of the patient health record stored in a table of the relational database. However, as it is often not known which table is to be searched for the term, the EHR typically constructs multiple SQL queries and executes the multiple SQL queries over different tables in the relational database that comprise the patient health record. Additionally or alternatively, the EHR may perform join operations on the different tables to form a joined table and the EHR may perform a SQL query over the joined table. Neither of these approaches are ideal, as performing multiple SQL queries and/or join operations may be computationally intensive and/or slow performing.

SUMMARY

The following is a brief summary of subject matter that is described in greater detail herein. This summary is not intended to be limiting as to the scope of the claims.

Described herein are various technologies pertaining to full textual search of a patient health record. More specifically, an electronic health records application (EHR) is described herein, wherein the EHR is a distributed application that includes server-side functionality (server EHR) and client-side functionality (client EHR). The EHR is configured to perform acts that enable textual search of a patient health record that is stored in one or more tables of a relational database.

In operation, a server EHR executing on a server computing device locates a patient health record for a patient stored in a table (or several tables) of a relational database based upon an identifier for the patient. For instance, the server EHR may execute a Structured Query Language (SQL) query to locate the patient health record in the relational database. Responsive to locating the patient health record, the server EHR generates a virtual patient object (VPO) for the patient based upon the patient health record stored in the table. The VPO may be an Extensible Markup Language (XML) file. The VPO comprises identifiers for clinical domains (e.g., encounters, problems, medications, etc.) and fields that are populated with data from the patient health record that corresponds to the clinical domains.

The server EHR generates computer-readable documents based upon the VPO. The documents comprise text corresponding to the data in the VPO. For instance, the server EHR may generate a document for each clinical domain represented in the VPO. Unlike the VPO, the documents do not include data that is not relevant to a textual search (e.g., certain types of metadata, formatting details, particular types of XML tags, etc.). The server EHR then causes a term-document index to be generated based upon the documents. The term-document index maps terms found in the text of the documents to identifiers for the documents in which the terms are found. For instance, if an allergies document contains the term "pollen", the term-document index includes the term "pollen" and an indication that the term "pollen" is included in the allergies document.

Subsequently, the server EHR receives a textual query from a client EHR executing on a client computing device that is in network communication with the server computing device. The textual query includes a term (e.g., "pollen"). Responsive to receiving the textual query, the server EHR executes a textual search over the term-document index based upon the textual query. The textual search produces search results, wherein the search results may comprise an identifier for a document in the documents that includes the term specified in the textual query.

The server EHR identifies a portion of the VPO (e.g., the allergies portion of the VPO) based upon the search results for the textual search, wherein the portion of the VPO includes the term specified in the textual query. For instance, in a first embodiment, the server EHR may identify the portion of the VPO based upon a previously created document-VPO index that maps the terms in the text of the documents to portions of the VPO corresponding to the terms. In a second embodiment, the term-document index comprises pointers to different portions of the VPO that include data that corresponds to the terms in the text of the documents, and as such the server EHR may identify the portion of the VPO based upon a pointer in the pointers. Responsive to identifying the portion of the VPO, the server EHR transmits the portion of the VPO to the client EHR, whereupon the client EHR presents the portion of the VPO within a graphical user interface (GUI) for the client EHR shown on a display.

The above-described technologies present various advantages over conventional technologies for performing searches over a patient health record. First, unlike conventional technologies, the above-described technologies enable full textual search of patient health records. Second, unlike conventional technologies, the above-described technologies do not require extensive SQL queries and/or join operations in order to locate a term in a patient health record. Furthermore, the above-described technologies may generate the documents and the term-document index prior to receiving the textual query (e.g., once a week), thus leading to improved search times when a textual search is performed.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE DRAWINGS

FIG. 4 is an illustration of an exemplary virtual patient object.

FIG. 5 is an illustration of a graphical user interface (GUI) that displays results of a full textual search of a patient health record.

DETAILED DESCRIPTION

Figure 1:
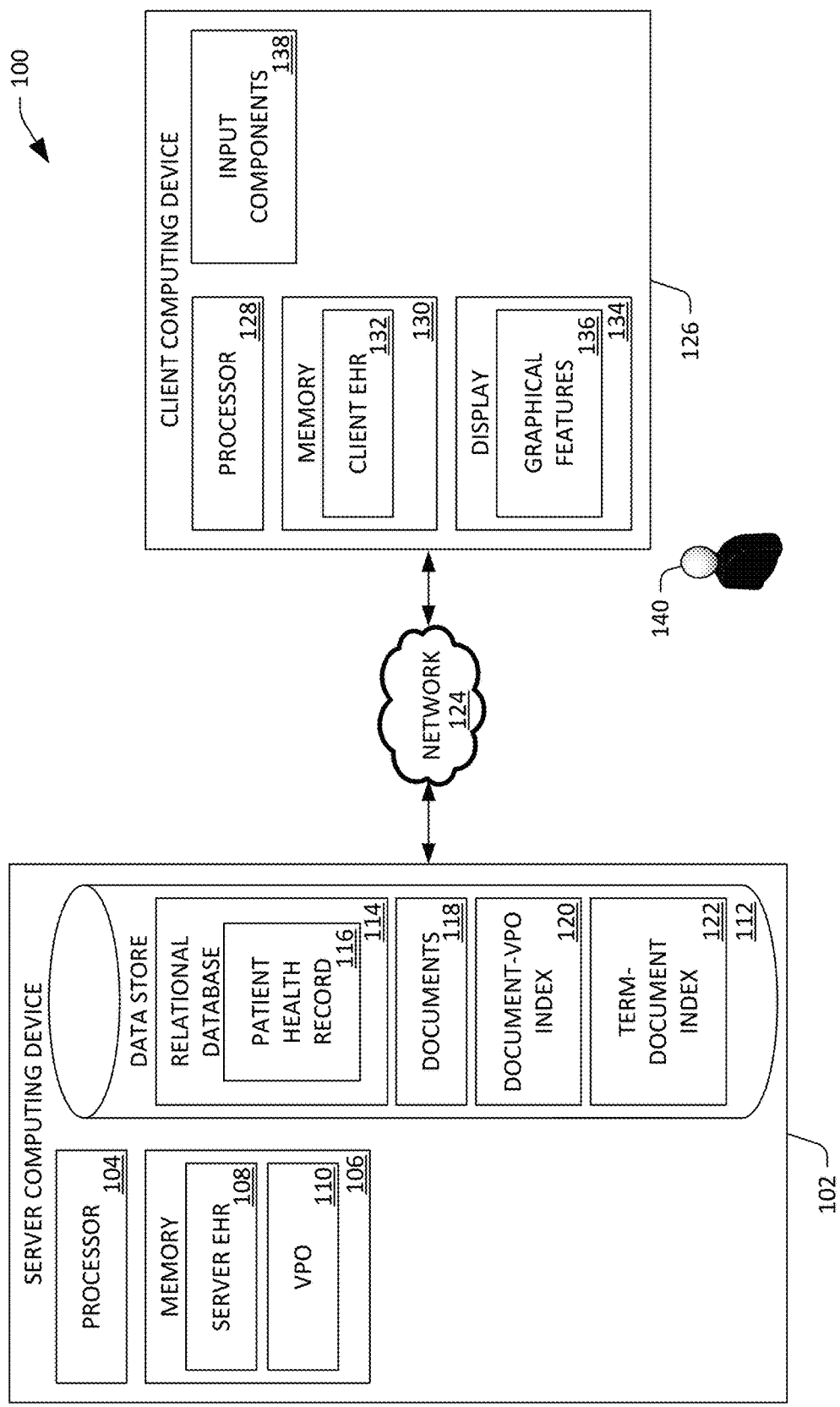
FIG. 1 is a functional block diagram of an exemplary computing system that facilitates full textual search of a patient health record.

Various technologies pertaining to full textual search of a patient health record are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component," "system," and "application" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

With reference to FIG. 1, an exemplary computing system 100 that facilitates full textual search of a patient health record is illustrated. The computing system 100 includes a server computing device 102. The server computing device 102 comprises a processor 104 and memory 106, wherein the memory 106 includes a server electronic health records application (server EHR) 108 and a virtual patient object (VPO) 110 loaded therein. In general, the server EHR 108 (when executed by the processor 104) is configured to perform a variety of programmatic tasks related to patient healthcare in a healthcare facility (e.g., patient intake, prescription generation, patient health record creation and maintenance, etc.). As will be described in greater detail below, the VPO 110 comprises identifiers for clinical domains and fields populated with data from a patient health record that corresponds to the clinical domains. The clinical domains comprise at least one of encounters, problems, past medical history, diagnoses, allergies, medications, measurements, labs, pathology, immunizations, imaging, procedures, and/or documents of the patient. The VPO 110 may represent the complete patient health record of the patient. The server EHR 108 utilizes the VPO 110 to facilitate care of the patient. For instance, the server EHR 108 may perform programmatic tasks utilizing the VPO 110 to facilitate care of the patient.

The server computing device 102 additionally comprises a data store 112. The data store 112 includes a relational database 114 that stores a patient health record 116 for a patient across one or more tables. For instance, the relational database 114 may be a database that is queried via Structured Query Language (SQL) queries. The patient health record 116 includes clinical data for the patient. The clinical data may include electronic health records, prescription records, claims data, patient/disease registries, health surveys data, clinical trials data, etc.

The data store 112 further includes (computer-readable) documents 118. As will be described in greater detail below, the documents 118 comprise computer-readable text that correspond to data from the VPO 110. Each document in the documents 118 may be assigned to a different clinical domain represented in the VPO 110. For instance, the documents 118 may include an encounters document, a problems document, and so forth. In an embodiment, the documents 118 may be text files (e.g., files with a .txt extension).

The data store 112 may include a document-VPO index 120. As will be described in greater detail below, the document-VPO index 120 maps terms in the text of the documents 118 to portions of the VPO 110 corresponding to the terms. The server EHR 108 utilizes the document-VPO index 120 to identify portions of the VPO 110 that include terms set forth in textual queries.

The data store 112 additionally includes a term-document index 122. As will be described in greater detail below, the term-document index 122 maps terms in the text of the documents 118 to identifiers for the documents 118 in which the terms are found. In an embodiment, the term-document index 122 includes pointers to different portions of the VPO 110 that include data corresponding to the text found in the documents 118.

The computing system 100 further includes a client computing device 126 operated by a healthcare worker 140. The client computing device 126 is in communication with the server computing device 102 by way of a network 124 (e.g., the Internet, intranet, etc.). In an example, the client computing device 126 may be a desktop computing device, a laptop computing device, a tablet computing device, a smartphone, etc.

The client computing device 126 comprises a processor 128 and memory 130, wherein the memory 130 has a client electronic health records application (client EHR) 132 loaded therein. In general, the client EHR 132 (when executed by the processor 128) is configured to communicate with the server EHR 108 in order to perform programmatic tasks related to patients in a healthcare facility. For instance, as will be described in greater detail below, the client EHR 132 may receive a textual query as input from the healthcare worker 140 and may cause a textual search to be performed over a patient health record based upon the textual query.

The client computing device 126 may include a display 134, whereupon graphical features 136 may be presented thereon. For instance, a graphical user interface (GUI) for the client EHR 132 may be presented on the display 134 as part of the graphical features 136. In an embodiment, the display 134 may be a touchscreen. The client computing device 126 includes input components 138 that enable the healthcare worker 140 to set forth input to the client computing device 126. For example, the input components 138 may include a mouse, a keyboard, a trackpad, a scroll wheel, a touchscreen, a camera, and/or a video camera. The client computing device 126 may also include speakers (not shown) as well as a data store (not shown).

Operation of the computing system 100 is now set forth. The server EHR 108 locates the patient health record 116 for the patient stored in a table (or more than one table) of the relational database 114 based upon an identifier for the patient. In an embodiment, the server EHR 108 executes a SQL query (or more than one SQL query) to locate the patient health record 116 for the patient. In an example, the server EHR 108 may receive the identifier for the patient from the client EHR 132.

Responsive to locating the patient health record 116, the server EHR 108 generates the VPO 110 for the patient based upon the patient health record 116. As discussed previously, the VPO 110 comprises identifiers for clinical domains and fields assigned to the clinical domains that are populated with data from the patient health record 116. As such, the server EHR 108 may extract entries of the table(s) in which the patient health record 116 is stored and populate the fields with data derived from the entries.

Subsequent to generating the VPO 110, the server EHR 108 generates the (computer-readable) documents 118 based upon the VPO 110. More specifically, the server EHR 108 may extract the data from the VPO 110 and format the data as text in the documents 118 such that the documents 118 comprise text corresponding to the data from the VPO 110. The documents 118 may fail to include certain portions of the VPO 110 that are not relevant for textual searches. For instance, the documents 118 may fail to include certain metadata from the VPO 110, formatting details, certain XML tags, etc.

In an embodiment, subsequent to generating the documents 118, the server EHR 108 generates the document-VPO index 120 based upon the documents 118 and the VPO 110. As described above, the document-VPO index 120 maps the terms in the text of the documents 118 to portions of the VPO 110 corresponding to the terms. The server EHR 108 may store the document-VPO index 120 in the data store 112.

The server EHR 108 causes the term-document index 122 to be generated based upon the documents 118. As described above, the term-document index 122 maps terms in the text of the documents 118 to identifiers for the documents 118 in which the terms are found. Thus, to generate the term-document index 122, the server EHR 108 may tokenize the content of each document in the documents 118, create a sorted list of each term in the text of the documents 118, and then list each document in which each term appears. In an embodiment, the server EHR 108 may omit common articles (e.g., the, a, an) and prepositions from the term-document index 122. The server EHR 108 may store the term-document index 122 in the data store 112.

In an embodiment, the server EHR 108 may generate the term-document index 122 based upon the VPO 110 as well. More specifically, the server EHR 108 may cause the term-document index 122 to include pointers to different portions of the VPO 110 that include data corresponding to the text found in the documents 118. Thus, in the embodiment, the server EHR 108 may identify portions of the VPO 110 that include a term specified in a textual query based upon the term-document index 122.

It is contemplated that the healthcare worker 140 is operating the client EHR 132. For instance, the client EHR 132 may be displaying a GUI on the display 134. The client EHR 132 receives a textual query from the healthcare worker 140 by way of the input components 138. The textual query comprises one or more terms that are to be searched for in the patient health record 116 (via the documents 118, the VPO 110, and the term-document index 122). In an example, the textual query may include the term "pollen." Responsive to receiving an indication from the healthcare worker 140, the client EHR 132 transmits the textual query to the server EHR 108.

Responsive to receiving the textual query from the client EHR 132, the server EHR 108 executes a textual search over the term-document index 122 based upon the textual query. The textual search produces search results that comprise an identifier for a document in the documents 118, the document including the term specified in the textual query. In the example above, the search results may comprise an identifier for an allergies document as the allergies document includes the term pollen.

Responsive to executing the search, the server EHR 108 identifies a portion of the VPO 110 that includes the term based upon search results for the textual search. In a first embodiment where the server EHR 108 has generated the document-VPO index 120, the server EHR 108 identifies the portion of the VPO 110 based upon the document-VPO index 120. More specifically, the server EHR 108 may locate the identifier for the document (that is in the search results) and the term in the document-VPO index 120. Using the identifier for the document, the term specified in the textual query, and the document-VPO index 120, the server EHR 108 identifies the portion of the VPO 110 that includes the term. In a second embodiment, the term-document index 122 includes pointers to different portions of the VPO 110 that include data corresponding to terms in the text of the document, and as such the server EHR 108 may identify the portion of the VPO 110 based upon a pointer in the term-document index 122.

Responsive to identifying the portion of the VPO 110, the server EHR 108 transmits the portion of the VPO 110 to the client EHR 132. Responsive to receiving the portion of the VPO 110, the client EHR 132 presents the portion of the VPO 110 on the display 134. For instance, the client EHR 132 may present the portion of the VPO 110 within a GUI for the client EHR 132 shown on the display 134.

In an embodiment, the client EHR 132 may be executed in a web browser. As such, the server EHR 108 may receive the textual query from the client EHR 132 as part of a Hypertext Transfer Protocol (HTTP) request (e.g., a GET request) generated via the client EHR 132. In an embodiment, generating the VPO 110, generating the documents 118, generating the document-VPO index 120, and generating the term-document index 122 may occur asynchronously to receiving the textual query described above.

Although the computing system 100 described above has been described as performing a textual search on a patient health record of a single patient, it is to be understood that the computing system 100 may perform textual searches on patient health records for many different patients. Additionally, although the patient health record 116 has been described and illustrated as being stored in the relational database 114, it is contemplated that the patient health record 116 may be stored in other types of databases as well. For instance, the patient health record may be stored in an object-oriented database, a graph database, a distributed database, a NoSQL database, etc. Furthermore, although the server EHR 108 has been described above as generating a document for each clinical domain, other options are contemplated. For instance, the server EHR 108 may generate several different documents for a single clinical domain or the server EHR 108 may generate a single document for all of the clinical domains.

Figure 2:
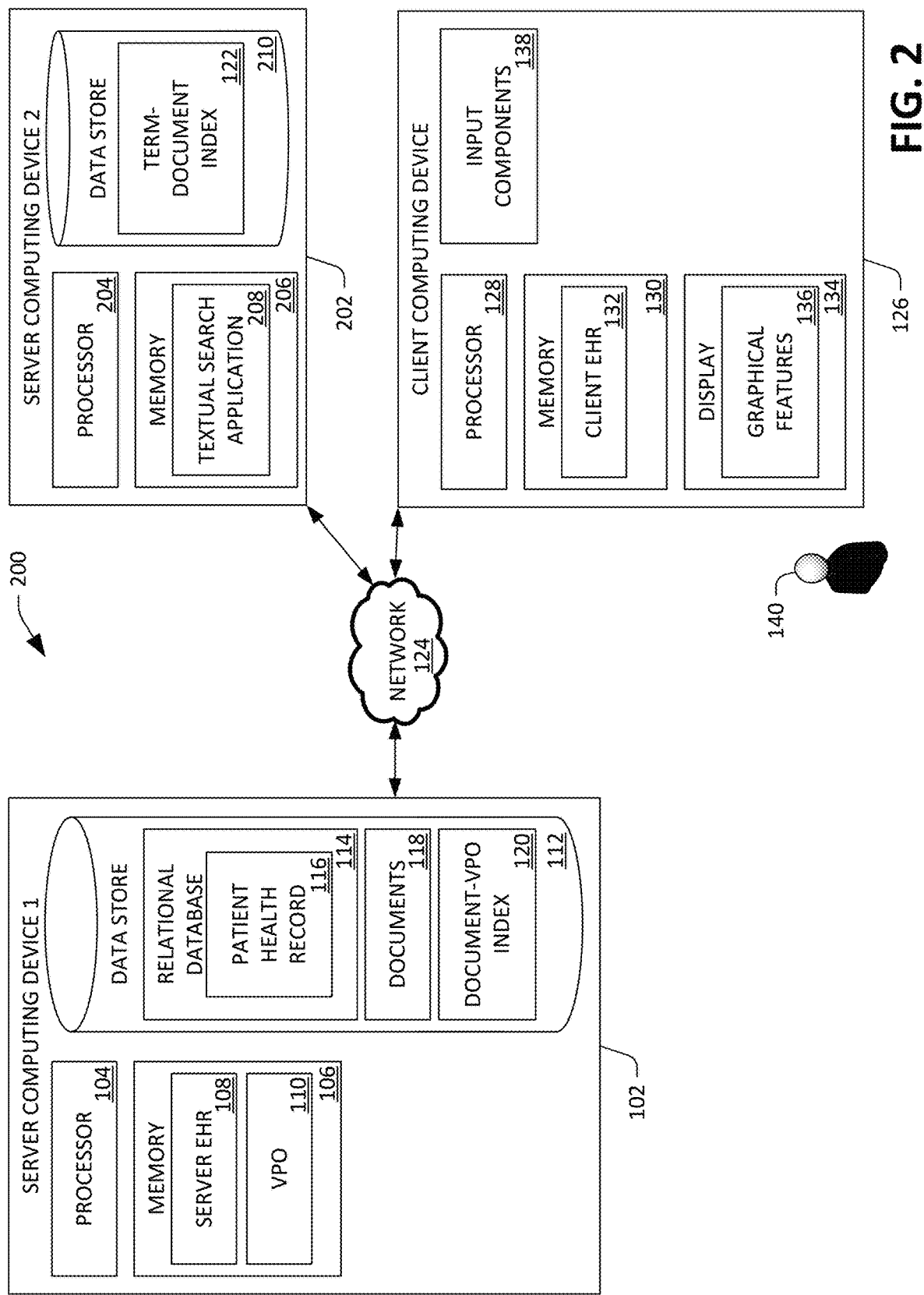
FIG. 2 is a functional block diagram of another exemplary computing system that facilitates full textual search of a patient health record.

Referring now to FIG. 2, an exemplary computing system 200 that facilitates full textual search of a patient health record is illustrated. The computing system 200 includes the server computing device 102 (now referred to as the first server computing device 102 for clarity) and its respective components described above in the description of FIG. 1 (e.g., the server EHR 108, the data store 112, and so forth). However, in the computing system 200, the data store 112 does not include the term-document index 122.

The computing system 200 further includes a second server computing device 202 that is in communication with the first server computing device 102 by way of the network 124 (or another network). The second server computing device 202 comprises a processor 204 and memory 206, wherein the memory 206 has a textual search application 208 loaded therein. The textual search application 208 is configured to generate the term-document index 122 (described above) based upon the documents 118 generated by the server EHR 108. Optionally, the textual search application 208 may generate the term-document index 122 based upon the VPO 110. The second server computing device 202 also comprises a data store 210 that stores the term-document index 122. In an embodiment, the second server computing device 202 may be a cloud computing platform.

The computing system 200 includes the client computing device 126 and its respective components (e.g., the client EHR 132, the display 134, and so forth) described above in the description of FIG. 1. In an embodiment, in addition to being in communication with the first server computing device 102, the client computing device 126 may be in communication with the second server computing device 202 by way of the network 124 (or another network).

The computing system 200 operates in a manner similar to that of the computing system 100 described above in the description of FIG. 1. For instance, the server EHR 108 generates the VPO 110, the documents 118, and (optionally) the document-VPO index 120 as described above. However, in the computing system 200, the server EHR 108 does not create the term-document index 122. Instead, subsequent to creating the documents 118, the server EHR 108 transmits the documents 118 (and optionally the VPO 110) to the textual search application 208. Responsive to receiving the documents 118, the textual search application 208 generates the term-document index 122 and stores the term-document index 122 in the data store 210.

When the server EHR 108 receives the textual query from the client EHR 132, the server EHR 108 transmits the textual query to the textual search application 208. Responsive to receiving the textual query, the textual search application 208 executes a textual search over the term-document index 122 stored in the data store 210. The textual search produces search results that may include an identifier for a term specified in the textual query. The textual search application 208 then transmits the search results to the server EHR 108, whereupon the server EHR 108 identifies a portion of the VPO 110 for the patient based upon the search results as described above in the description of FIG. 1. The server EHR 108 then causes the portion of the VPO 110 to be presented on the display 134 of the client computing device 126 as described above.

Figure 3:
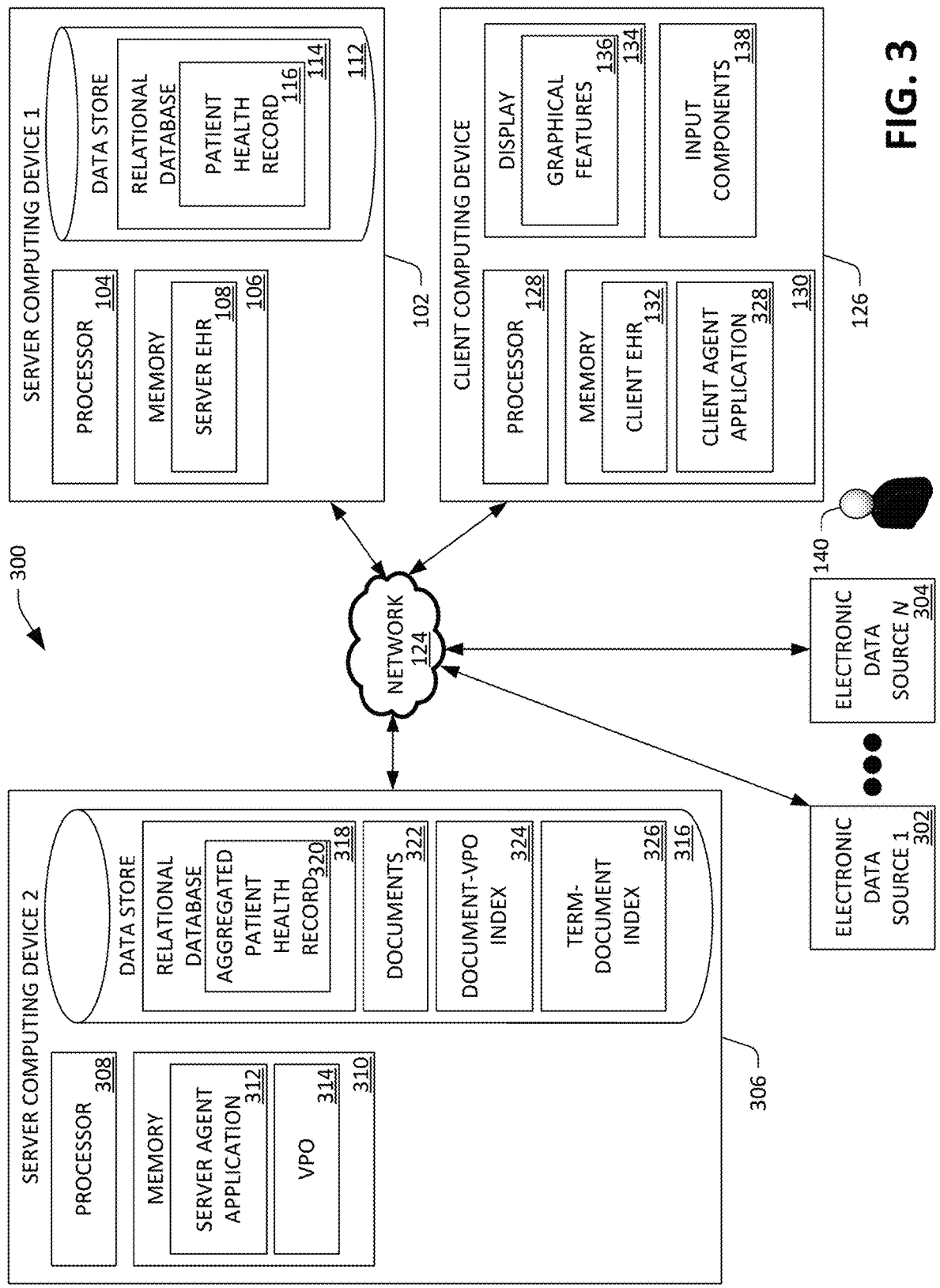
FIG. 3 is a functional block diagram of yet another exemplary computing system that facilitates full textual search of a patient health record.

Turning now to FIG. 3, an exemplary computing system 300 that facilitates full textual search of a patient health record is illustrated. The computing system 300 includes a first electronic data source 302 and an Nth electronic data source 304, where N is a positive integer larger than one (collectively, "the plurality of electronic data sources 302-304). The plurality of electronic data sources 302-304 may include server EHRs (in addition to the server EHR 108), Health Information Exchanges (HIEs), patient portal applications, etc.

The computing system 300 includes the server computing device 102 described above in the description of FIG. 1 (now referred to as "the first server computing device 102" for clarity) and its respective components (e.g., the server EHR 108, the relational database 114, and so forth). However, in the computing system 300, the memory 106 of the first server computing device 102 may not include a VPO, nor does the data store 112 include documents, a document-VPO index, or a term-document index.

The computing system 300 further includes a second server computing device 306. The second server computing device 306 is in communication with the plurality of electronic data sources 302-304, the first server computing device 102, and/or the client computing device 126 by way of the network 124 (or several different networks). The second server computing device 306 comprises a processor 308 and memory 310, wherein the memory 310 has a server agent application 312 and a VPO 314 loaded therein. In general, the server agent application 312 (when executed by the processor 308) is configured to retrieve and aggregate patient health records from the plurality of electronic data sources 302-304 (as opposed to patient health records from a single source, as with the server EHR 108). The VPO 314 is similar to the VPO 110 described above in the description of FIG. 1, that is, the VPO 314 comprises identifiers for clinical domains and fields assigned to the clinical domains that are populated with data from patient health records; however, unlike the VPO 110, the data populating the fields in the VPO 314 originates from the plurality of electronic data sources 302-304 (as opposed to a single source maintained by the server EHR 108).

The computing system 300 includes a data store 316. The data store 316 comprises a relational database 318 (e.g., a SQL database) that stores an aggregated patient health record 320 that has been aggregated from the plurality of electronic data sources 302-304. Documents 322, document-VPO index 324, and term-document index 326 are similar to the documents 118, the document-VPO index 120, and the term-document index 122, respectively, except that they are generated based upon the aggregated patient health record 320 instead of the patient health record 116.

The computing system 300 includes the client computing device 126 and its respective components (e.g., the client EHR 132, the display 134, and so forth) described above in the description of FIG. 1. The client computing device 126 is in network communication with the first server computing device 102 and the second server computing device 306 by way of the network 124 (or by separate networks). In the computing system 300, the memory 130 of the client computing device 126 has a client agent application 328 loaded therein. In general, the client agent application 328 (when executed by the processor 128) is configured to communicate with the server agent application 312 in order to retrieve and display patient health records from the plurality of electronic data sources 302-304. In an embodiment, the client agent application 328 may execute simultaneously with the client EHR 132. For instance, the client agent application 328 may present a GUI on the display 134 that overlays a GUI for the client EHR 132.

The computing system 300 operates in a manner similar to the computing system 100 described above in the description of FIG. 1. However, unlike the VPO 110 utilized in the computing system 100, the VPO 314 represents the patient health record as aggregated from the plurality of electronic data sources 302-304. Additionally, unlike the computing system 100 described in FIG. 1, the server agent application 312 performs the full textual search over the aggregated patient health record 320 (in a manner as described above in the description of FIG. 1). For instance, the server agent application 312 generates the VPO 314, the documents 322, the term-document index 326, and (optionally) the document-VPO index 324 as described above in the description of FIG. 1. The server agent application 312 also receives the textual query from the client agent application 328, executes the search over the term-document index 326 based upon the textual query, and identifies the portion of the VPO 314 based upon search results for their search (either by utilizing the document-VPO index 324 or the term-document index 326). Moreover, unlike the computing system 100, the client agent application 328 receives the portion of the VPO 314 from the server agent application 312 and presents the portion of the VPO 314 within a GUI for the client agent application 328 shown on the display 134.

Referring now to FIG. 4, a portion of an exemplary VPO 400 is illustrated. In an example, the VPO 400 may be the VPO 110 described above or the VPO 110 may be the VPO 400. In another example, the VPO 400 may be the VPO 314 described above or the VPO 314 may be the VPO 400. As shown in in FIG. 4, the VPO 400 is an XML file that comprises XML tags (e.g., "<id>", "</id>", etc.). When the server EHR 108 generates documents from the VPO 400, the server EHR 108 may remove the XML tags from the VPO 400 (as well as other information) such that the documents comprise text that is relevant to textual searches. In an example, the server EHR 108 may extract the "Allergy to Pollen" portion of the VPO 400 while discarding the remaining portions of the VPO 400.

With reference now to FIG. 5, a GUI 500 that displays results of a full textual search of a patient health record is illustrated. The GUI 500 may be a GUI for the client EHR 132 or a GUI for the client agent application 328. As depicted in FIG. 5, the GUI 500 displays demographic information of a patient. The GUI 500 also includes identifiers for different clinical domains (e.g., encounters, problems, and so forth). The identifiers for the clinical domains are selectable and display further information belonging to the clinical domain when selected. The GUI 500 includes a search bar that enables the healthcare worker 140 to set forth a textual query. In the example shown in FIG. 5, the healthcare worker 140 has set forth the term "pollen" as a textual query. The GUI 500 also include view options. The view options enable certain clinical domains to be filtered from the GUI 500. In the GUI 500, identifiers for clinical domains that include the term in the textual query may be highlighted. For instance, as the allergies clinical domain includes the term in the textual query ("pollen"), the identifier for the allergies clinical domain is highlighted in the GUI 500. Furthermore, the GUI 500, the term may also be highlighted with the GUI. For instance, the term "pollen" is highlighted in the portion of the VPO that includes the term specified in the textual query. Additionally, data within the clinical domains that is not recent may be filtered from view in the view options as well.

Figure 6:
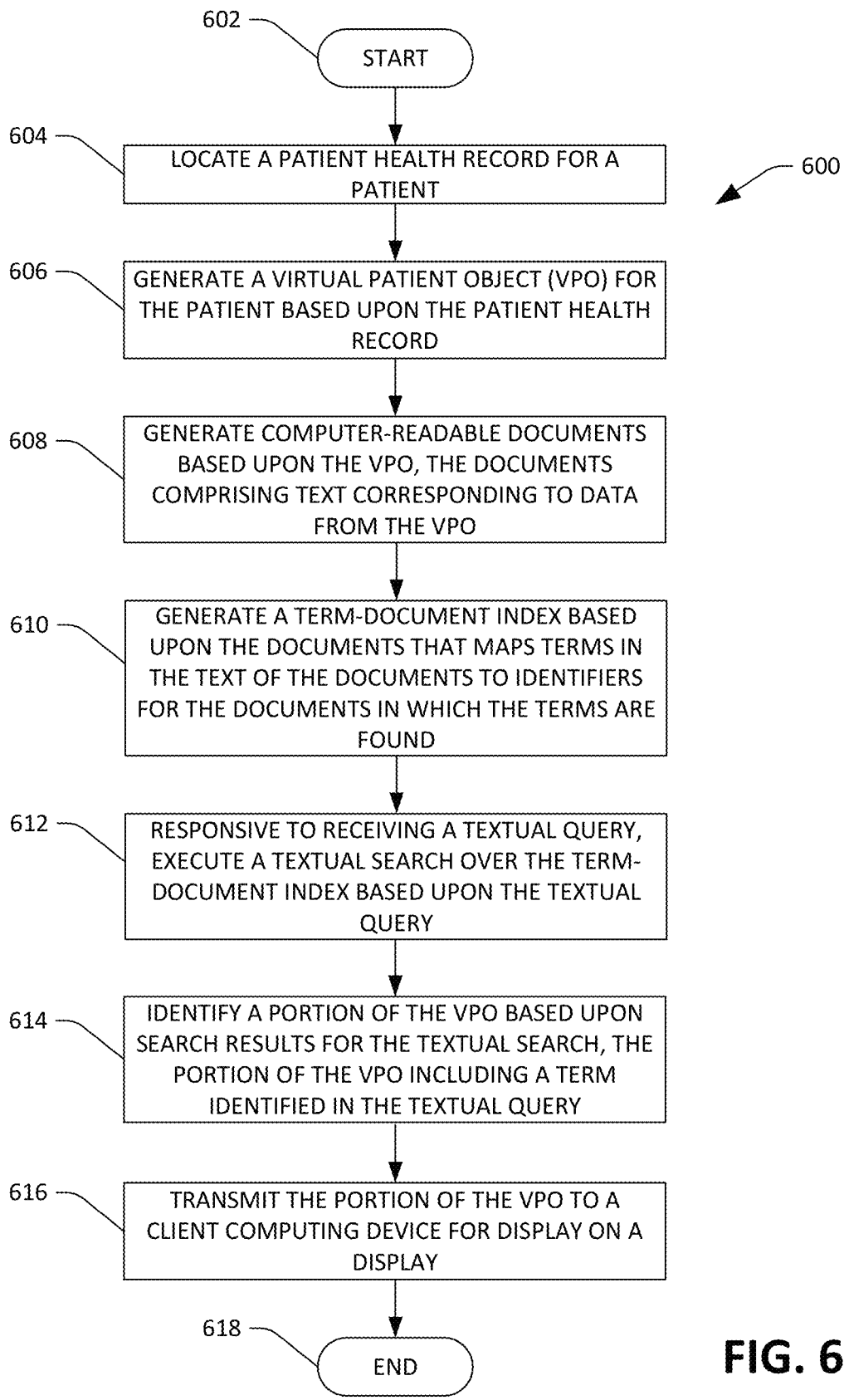
FIG. 6 is a flow diagram that illustrates an exemplary methodology executed by a server electronic health records application that facilitates a full textual search of a patient health record.
Figure 7:
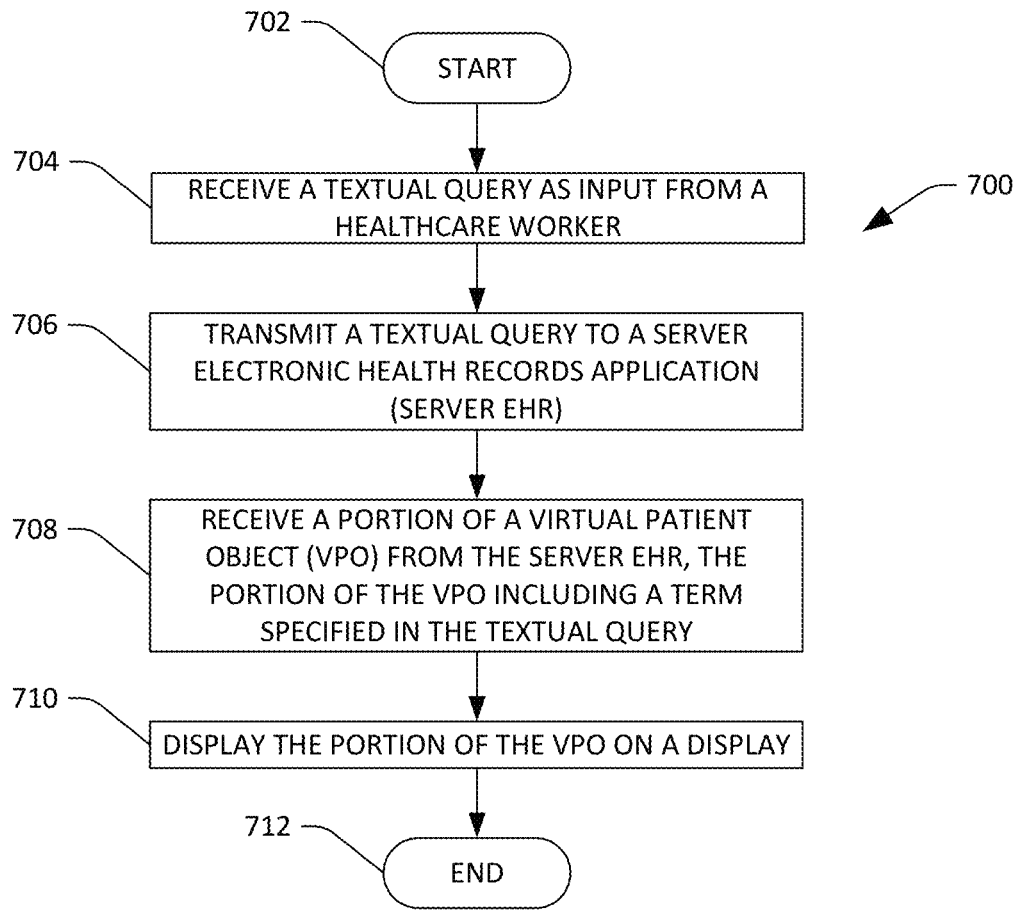
FIG. 7 is a flow diagram that illustrates an exemplary methodology executed by a client electronic health records application that facilitates a full textual search of a patient health record.

FIGS. 6 and 7 illustrate exemplary methodologies relating to full textual search of a patient health record. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Referring now to FIG. 6, a methodology 600 executed by a server EHR that facilitates full textual search of a patient health record is illustrated. The methodology 600 begins at 602, and at 604, the server EHR locates a patient health record for the patient stored in a table of a relational database. At 606, the server EHR generates a VPO for the patient based upon the patient health record stored in the table of the relational database. The VPO comprises identifiers for clinical domains and fields assigned to the clinical domains. The fields are populated with data from the patient health record that corresponds to the clinical domains.

At 608, the server EHR generates computer-readable documents based upon the VPO. The documents comprise text corresponding to the data from the VPO. For instance, each document in the documents may correspond to a different clinical domain in the clinical domains represented by the VPO. At 610, the server EHR generates a term-document index based upon the documents. The term-document index maps terms in the text of the documents to identifiers for the documents in which the terms are found.

At 612, responsive to receiving a textual query from a client EHR, the server EHR executes a textual search over the term-document index based upon the textual query. The textual search produces search results, wherein the search results include an identifier for a document in the documents that includes a term specified in the textual query. At 614, the server EHR identifies a portion of the VPO for the patient based upon the search results for the textual search. The portion of the VPO for the patient includes the term specified in the textual query. At 616, the server EHR transmits the portion of the VPO to the client EHR. The client EHR then presents the portion of the VPO on the display. The methodology 600 concludes at 618.

Turning now to FIG. 7, a methodology 700 executed by a client EHR that facilitates full textual search of a patient health record is illustrated. The methodology 700 begins at 702, and at 704, the client EHR receives a textual query as input from a healthcare worker. At 706, responsive to receiving an indication from the healthcare worker, the client EHR transmits the textual query to a server EHR. At 708, the client EHR receives a portion of the VPO from the server EHR. The portion of the VPO includes a term included in the textual query. At 710, the client EHR displays the portion of the VPO on a display. The methodology 700 concludes at 712.

Figure 8:
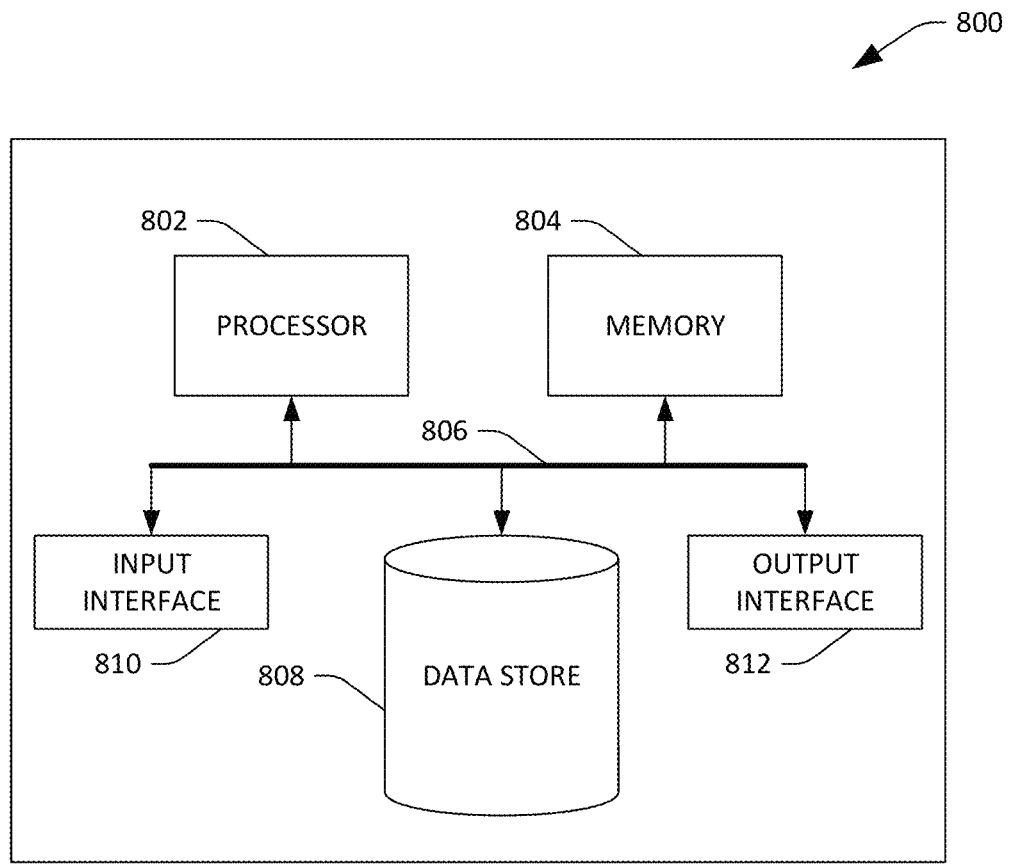
FIG. 8 is an exemplary computing system.

Referring now to FIG. 8, a high-level illustration of an exemplary computing device 800 that can be used in accordance with the systems and methodologies disclosed herein is illustrated. For instance, the computing device 800 may be used in a system that supports full textual search of a patient health record. By way of another example, the computing device 800 can be used in a system that generates VPOs from patient health records stored in tables of a relational database. The computing device 800 includes at least one processor 802 that executes instructions that are stored in a memory 804. The instructions may be, for instance, instructions for implementing functionality described as being carried out by one or more components discussed above or instructions for implementing one or more of the methods described above. The processor 802 may access the memory 804 by way of a system bus 806. In addition to storing executable instructions, the memory 804 may also store patient health records, VPOs, documents, document-VPO indices, term-document indices, etc.

The computing device 800 additionally includes a data store 808 that is accessible by the processor 802 by way of the system bus 806. The data store 808 may include executable instructions, patient health records, VPOs, documents, document-VPO indices, term-document indices, etc. The computing device 800 also includes an input interface 810 that allows external devices to communicate with the computing device 800. For instance, the input interface 810 may be used to receive instructions from an external computer device, from a user, etc. The computing device 800 also includes an output interface 812 that interfaces the computing device 800 with one or more external devices. For example, the computing device 800 may display text, images, etc. by way of the output interface 812.

It is contemplated that the external devices that communicate with the computing device 800 via the input interface 810 and the output interface 812 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 800 in a manner free from constraints imposed by input devices such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 800 may be a distributed system. Thus, for instance, several devices may be in communication by way of a network connection and may collectively perform tasks described as being performed by the computing device 800.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A server computing device, comprising:
   a processor; and
   memory storing instructions that, when executed by the processor, cause the processor to perform acts comprising:
      locating a patient health record for a patient stored in a table of a relational database based upon an identifier for the patient;
      generating a virtual patient object (VPO) for the patient based upon the patient health record, wherein the VPO for the patient comprises identifiers for clinical domains and fields assigned to the clinical domains, wherein the fields are populated with data from the patient health record that corresponds to the clinical domains;
      generating computer-readable documents based upon the VPO, the documents comprising text corresponding to the data from the VPO;
      causing a term-document index to be generated based upon the documents, wherein the term-document index maps terms in the text of the documents to identifiers for the documents in which the terms are found;
      responsive to receiving a textual query from a client computing device that is in network communication with the server computing device, executing a textual search over the term-document index based upon the textual query, wherein the textual search produces search results that comprise an identifier for a document in the documents that includes a term specified in the textual query;
      identifying a portion of the VPO for the patient based upon the search results for the textual search, wherein the portion of the VPO for the patient includes the term specified in the textual query; and
      transmitting the portion of the VPO to the client computing device, wherein the client computing device presents the portion of the VPO on a display.

2. The server computing device of claim 1, the acts further comprising:
   prior to locating the patient health record for the patient, receiving the identifier for the patient from the client computing device.

3. The server computing device of claim 1, the acts further comprising:
   subsequent to generating the documents, generating a document-VPO index based upon the documents and the VPO, wherein the document-VPO index maps the terms in the text of the documents to portions of the VPO corresponding to the terms, wherein identifying the portion of the VPO for the patient is further based upon the document-VPO index.

4. The server computing device of claim 1, wherein generating the documents based upon the VPO comprises extracting the data from the VPO and formatting the data as the text in the documents.

5. The server computing device of claim 1, wherein the relational database is stored in a data store accessible by the server computing device, wherein the VPO is stored in the memory.

6. The server computing device of claim 1, wherein the instructions comprise an electronic health records application.

7. The server computing device of claim 1, wherein the clinical domains comprise at least one of:
   encounters;
   problems;
   past medical history;
   diagnoses;
   allergies;
   medications;
   measurements;
   labs;
   pathology;
   immunizations;
   imaging;
   procedures; or
   documents of the patient.

8. The server computing device of claim 1, wherein the term is highlighted in the portion of the VPO presented on the display.

9. The server computing device of claim 1, wherein the VPO for the patient is an Extensible Markup Language (XML) file.

10. The server computing device of claim 1, wherein an identifier for a clinical domain in the VPO to which the term pertains is highlighted in the portion of the VPO presented on the display.

11. A method executed by a processor of a server computing device while the processor executes a server electronic health records application (server EHR), comprising:
   locating a patient health record for a patient stored in a table of a relational database;
   generating a virtual patient object (VPO) for the patient based upon the patient health record, wherein the VPO for the patient comprises identifiers for clinical domains and fields assigned to the clinical domains, wherein the fields are populated with data from the patient health record that corresponds to the clinical domains;
   generating computer-readable documents based upon the VPO, the documents comprising text corresponding to the data from the VPO;
   generating a term-document index based upon the documents, wherein the term-document index maps terms in the text of the documents to identifiers for the documents in which the terms are found;
   responsive to receiving a textual query from a client electronic health records application (client EHR) executing on a client computing device that is in network communication with the server computing device, executing a textual search over the term-document index based upon the textual query, wherein the textual search produces search results that comprise an identifier for a document in the documents that includes a term specified in the textual query;
   identifying a portion of the VPO for the patient based upon the search results for the textual search, wherein the portion of the VPO for the patient includes the term specified in the textual query; and
   transmitting the portion of the VPO to the client EHR, wherein the client EHR presents the portion of the VPO on a display.

12. The method of claim 11, wherein locating the patient health record, generating the VPO, generating the documents, and generating the term-document index occur asynchronously to receiving the textual query from the client EHR.

13. The method of claim 11, wherein each document in the documents is assigned to a different clinical domain in the clinical domains.

14. The method of claim 11, wherein the client EHR receives the textual query as input from a healthcare worker operating the client computing device, wherein the client EHR transmits the textual query to the server EHR responsive to receiving an indication from the healthcare worker.

15. The method of claim 11, wherein locating the patient health record for the patient comprises executing a Structured Query Language (SQL) query comprising the identifier for the patient.

16. The method of claim 11, wherein the term-document index is further generated based upon the VPO, wherein the term-document index comprises pointers to portions of the VPO that include data corresponding to the terms in the text of the documents, wherein identifying the portion of the VPO is based upon a pointer in the pointers that points to the portion of the VPO.

17. A computer-readable storage medium comprising instructions that, when executed by a processor, cause the processor to perform acts comprising:
  generating a virtual patient object (VPO) for a patient based upon a patient health record stored in a table of a relational database, wherein the VPO for the patient comprises identifiers for clinical domains and fields assigned to the clinical domains, wherein the fields are populated with data from the patient health record that corresponds to the clinical domains;
  generating computer-readable documents based upon the VPO, the documents comprising text corresponding to the data from the VPO;
  generating a document-VPO index based upon the documents and the VPO, wherein the document-VPO index maps terms in the text of the documents to portions of the VPO corresponding to the terms;
  causing a term-document index to be generated based upon the documents, wherein the term-document index maps the terms in the text of the documents to identifiers for the documents in which the terms are found;
  responsive to receiving a textual query from a client computing device that is in network communication with the server computing device, executing a textual search over the term-document index based upon the textual query, wherein the textual search produces search results that comprise an identifier for a document in the documents that includes a term specified in the textual query;
  identifying a portion of the VPO for the patient based upon the search results for the textual search and the document-VPO index, wherein the portion of the VPO for the patient includes the term specified in the textual query; and
  transmitting the portion of the VPO to the client computing device, wherein the client computing device presents the portion of the VPO on a display.

18. The computer-readable storage medium of claim 17, wherein the client computing device executes an application in a web browser, wherein the server computing device receives the textual query from the application as part of a Hypertext Transfer Protocol (HTTP) request generated by the application.

19. The computer-readable storage medium of claim 17, wherein the documents are text files.

20. The computer-readable storage medium of claim 17, wherein the patient health record comprises data maintained by a server electronic health records application (server EHR) and data from a plurality of electronic data sources external to the server EHR.

* * * * *